US011464473B2

(12) United States Patent
Madabhushi et al.

(10) Patent No.: US 11,464,473 B2
(45) Date of Patent: Oct. 11, 2022

(54) DISTINGUISHING MINIMALLY INVASIVE CARCINOMA AND ADENOCARCINOMA IN SITU FROM INVASIVE ADENOCARCINOMA WITH INTRATUMORAL AND PERI-TUMORAL TEXTURAL FEATURES

(71) Applicant: Case Western Reserve University, Cleveland, OH (US)

(72) Inventors: Anant Madabhushi, Shaker Heights, OH (US); Pranjal Vaidya, Cleveland, OH (US); Kaustav Bera, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 851 days.

(21) Appl. No.: 16/361,667

(22) Filed: Mar. 22, 2019

(65) Prior Publication Data

US 2019/0357870 A1 Nov. 28, 2019

Related U.S. Application Data

(60) Provisional application No. 62/675,899, filed on May 24, 2018.

(51) Int. Cl.
*A61B 6/00* (2006.01)
*G06T 7/00* (2017.01)
(Continued)

(52) U.S. Cl.
CPC ............ *A61B 6/5217* (2013.01); *A61B 6/032* (2013.01); *A61B 6/50* (2013.01); *G06K 9/6228* (2013.01);
(Continued)

(58) Field of Classification Search
CPC ......... A61B 6/032; A61B 6/50; A61B 6/5217; G06K 9/6228; G06K 9/6234;
(Continued)

(56) References Cited

U.S. PATENT DOCUMENTS

| 2016/0155225 | A1* | 6/2016 | Madabhushi | ......... | G06T 7/0012 |
| | | | | | 382/131 |
| 2016/0196648 | A1* | 7/2016 | Madabhushi | ........... | A61P 37/06 |
| | | | | | 382/131 |
| 2017/0039737 | A1* | 2/2017 | Madabhushi | .......... | G06V 10/44 |

\* cited by examiner

*Primary Examiner* — Amelie R Davis

(74) *Attorney, Agent, or Firm* — Eschweiler & Potashnik, LLC

(57) ABSTRACT

Embodiments include controlling a processor to access a radiological image of a region of lung tissue, where the radiological image includes a ground glass (GGO) nodule; define a tumoral region by segmenting the GGO nodule, where defining the tumoral region includes defining a tumoral boundary; define a peri-tumoral region based on the tumoral boundary; extract a set of radiomic features from the peri-tumoral region and the tumoral region; provide the set of radiomic features to a machine learning classifier trained to distinguish minimally invasive adenocarcinoma (MIA) and adenocarcinoma in situ (AIS) from invasive adenocarcinoma; receive, from the machine learning classifier, a probability that the GGO nodule is invasive adenocarcinoma, where the machine learning classifier computes the probability based on the set of radiomic features; generate a classification of the GGO nodule as MIA or AIS, or invasive adenocarcinoma, based, at least in part, on the probability; and display the classification.

20 Claims, 12 Drawing Sheets

(51) Int. Cl.
*G06K 9/62* (2022.01)
*A61B 6/03* (2006.01)
*G16H 30/40* (2018.01)
*G06N 20/00* (2019.01)
*G06T 7/12* (2017.01)

(52) U.S. Cl.
CPC ......... *G06K 9/6234* (2013.01); *G06K 9/6262* (2013.01); *G06K 9/6277* (2013.01); *G06N 20/00* (2019.01); *G06T 7/0012* (2013.01); *G06T 7/12* (2017.01); *G16H 30/40* (2018.01); *G06T 2207/10081* (2013.01); *G06T 2207/20076* (2013.01); *G06T 2207/20081* (2013.01); *G06T 2207/30064* (2013.01); *G06T 2207/30096* (2013.01)

(58) Field of Classification Search
CPC .. G06K 9/6262; G06K 9/6271; G06K 9/6277; G06N 20/00; G06T 2207/10081; G06T 2207/20076; G06T 2207/20081; G06T 2207/30064; G06T 2207/30096; G06T 7/0012; G06T 7/12; G06T 7/41; G06V 10/454; G06V 2201/03; G16H 20/10; G16H 30/40; G16H 50/20
See application file for complete search history.

DISTINGUISHING MINIMALLY INVASIVE CARCINOMA AND ADENOCARCINOMA IN SITU FROM INVASIVE ADENOCARCINOMA WITH INTRATUMORAL AND PERI-TUMORAL TEXTURAL FEATURES

CROSS REFERENCE TO RELATED APPLICATIONS

This application claims the benefit of U.S. Provisional Application 62/675,899 filed May 24, 2018, which is incorporated by reference herein in its entirety.

FEDERAL FUNDING NOTICE

This invention was made with government support under CA199374, CA202752, CA208236, CA216579, CA220581 awarded by the National Institutes of Health and W81XWH-14-1-0323, W81XWH-18-1-0440 awarded by the Department of Defense. The government has certain rights in the invention.

BACKGROUND

Lepidic cancers follow an orderly progression from adenocarcinoma in situ (AIS) to minimally invasive carcinoma (MIA) to invasive adenocarcinoma (INV). With the popularization of low-dose computed tomography (LDCT) screening for lung cancer, the frequency of reported small-sized carcinoma appearing as pulmonary ground glass opacity (GGO) nodules is increasing in routine clinical practice. The presence of a nodular component on computed tomography (CT) imagery suggests an invasive component, but neither existing CT approaches nor needle biopsy can actually distinguish invasive disease in early lepidic lesions.

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
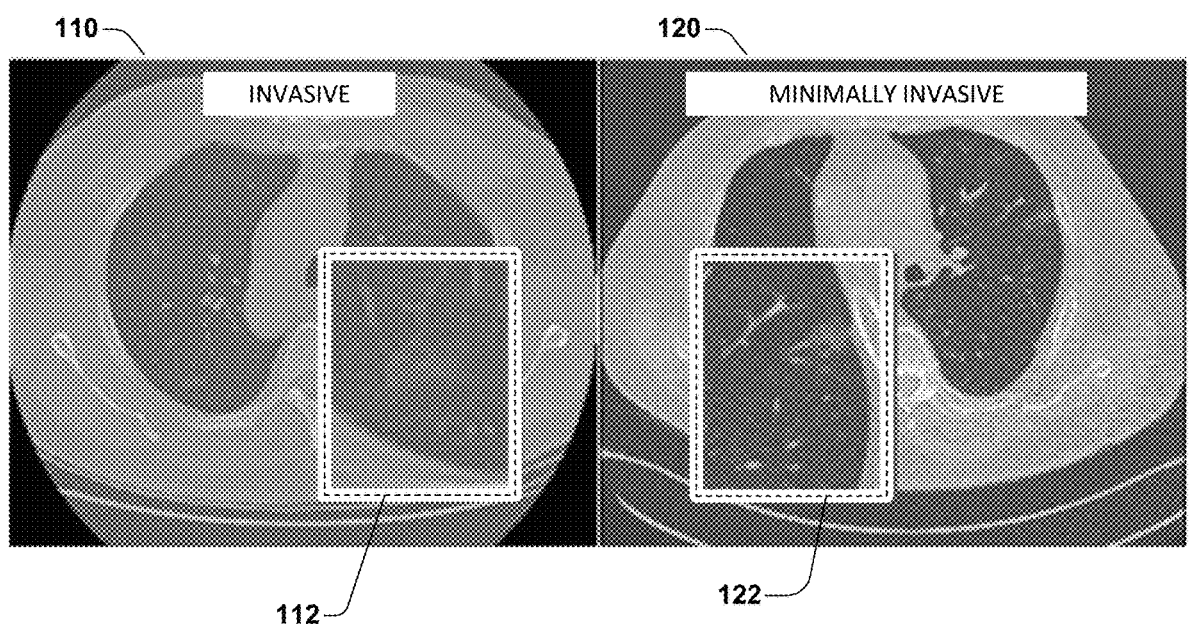
FIG. 1 illustrates CT scans of ground-glass tumor regions for invasive adenocarcinoma and minimally invasive adenocarcinoma (MIA).

Stage IA lung cancer cases include those having a tumor of less than 3 cm in diameter. Although stage 1A is not considered as destructive as some higher stage cancers, the five-year survival rate is 49% and sometimes these patients have recurrent disease even after curative surgery. In contrast, the rate of five-year disease-free survival of low grade adenocarcinoma has been evaluated as 100% of adenocarcinoma in situ (AIS) and nearly 100% disease-specific survival of minimally invasive adenocarcinoma (MIA). The presence of a nodular component on computed tomography (CT) imagery suggests an invasive component, but neither existing CT approaches nor needle biopsy can accurately differentiate invasive disease in early lepidic lesions. Additionally, on frozen tissue samples, it is difficult to distinguish AIS or MIA nodules from invasive adenocarcinoma, and consequently invasive adenocarcinoma is overestimated or over-diagnosed. Tissue analysis also requires examination of the entire tumor region to rule out invasive component which makes it additionally challenging. Thus an improved, non-invasive technique for distinguishing AIS or MIA nodules from invasive adenocarcinoma would be advantageous.

Embodiments construct a non-invasive biomarker using radiomic features extracted from CT imagery of tissue demonstrating lung nodules, including lung cancer pathology. Radiomics is the extraction of high-throughput quantitative imaging data from medical images to investigate hidden patterns from a region of interest (ROI). In the lung cancer domain, existing approaches typically involve examining an ROI inside the tumor region. Some existing approaches may consider examining the peri-tumoral region. The tumor microenvironment and habitat may include valuable disease specific prognostic cues. For example, peri-tumoral lymphatic microvessel density (LMVD) may be correlated with poor prognosis in NSCLC. In another example, specimens of non-small cell lung cancer (NSCLC) histology may have higher numbers of tumor-associated inflammatory cells (TAIC) in the peri-tumoral compartment when compared to the intra-tumoral region, while a higher number of TAIC cells may be associated with improved recurrence free survival.

Embodiments extract radiomic features from the inside (intratumoral) and outside (peri-tumoral) tumoral regions to differentiate MIA and AIS from invasive (INV) adenocarcinoma regions represented on medical imagery, including CT scans. Embodiments may analyze T1a INV nodules (predominantly GGO<=2 cm diameter), matching with the MIA and AIS subset (<=2 cm diameter) of nodules.

In one embodiment, a set of 146 CT scans from four different institutions was accessed. Only T1a INV cancer cases were chosen (predominantly GGO<=2 cm diameter) from the entire cohort, matching the diameter of the MIA and AIS subset. The first data set (N=39) which contained 7 AIS and 2 MIA and 30 INV cancer cases was used for training a machine learning classifier. The remaining cases (N=108) were used as an independent validation set and were kept blinded to the training model. All patients were divided into two groups: a pre-invasive/minimally invasive lesion group (AIS, MIA) and a frank invasive group. These two groups were used as clinical endpoints for the classification.

Embodiments may segment lung nodules represented on CT imagery. FIG. 1 illustrates CT imagery of GGO regions. A CT image of an ROI including an invasive GGO nodule is illustrated at 110, with a magnified region of the invasive GGO nodule illustrated at 112. A CT image of an ROI including a minimally invasive GGO nodule is illustrated at 120, with a magnified region of the minimally invasive GGO nodule illustrated at 122. In one embodiment, tumors (i.e., nodules) may be annotated by an expert radiologist using 3D-slicer software and an annotation tool. In another embodiment, automated segmentation techniques may be employed. For example, in one embodiment, lung nodules are automatically segmented from non-lung nodule tissue using a watershed segmentation technique, a region growing segmentation technique, an active contour technique, or a convolutional neural network (CNN). In this example, members of the set of 146 CT scans had varying slice thicknesses, where a member of the set of 146 CT scans may have a slice thickness of between 1 mm to 5 mm. The index lesions were identified using patient reports. These nodules were used to estimate the intra-tumoral and peri-tumoral texture features. The peri-tumoral compartment around the nodule was defined via the use of quantitative morphological operations (dilation) as a region extending radially from the nodule boundary up to, in one embodiment, 15 mm. Embodiments may eliminate the effect of skin, air, or lipids when the mask is extended. When defining the peritumoral region, embodiments may preprocess the CT imagery, including analyzing CT Hounsfield units to avoid the chest wall, cardiothoracic cavity and the areas around the lung parenchyma for more accurate analysis.

Figure 2:
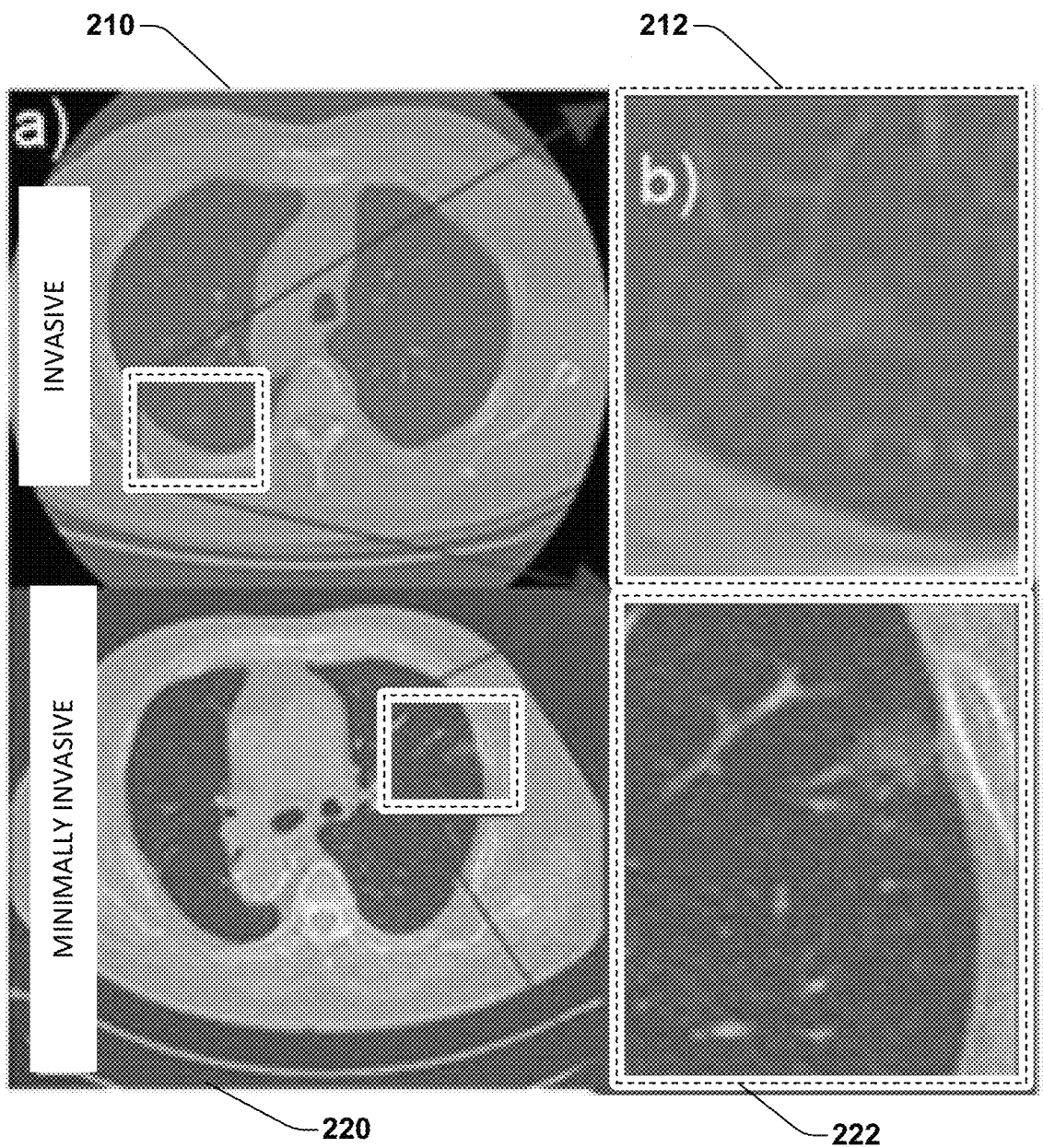
FIG. 2 illustrates CT scans of GGO regions for invasive adenocarcinoma and MIA.
Figure 3:
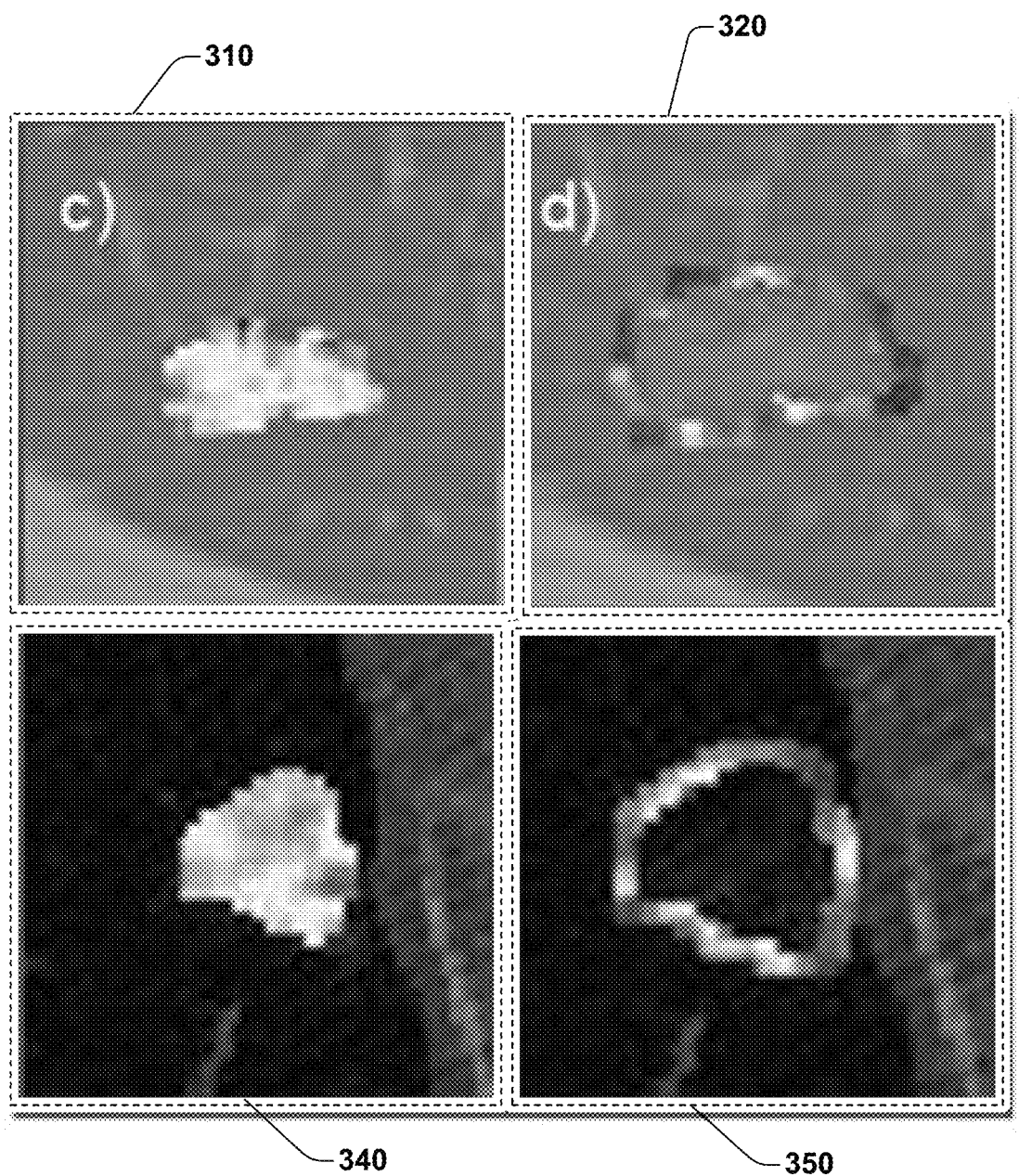
FIG. 3 illustrates intratumoral co-occurrence of local anisotropic gradient orientations (CoLlAGE) textural features and 0-3 mm peri-tumoral CoLlAGE features in CT scans of GGO regions for invasive adenocarcinoma and MIA.

Embodiments extract radiomic features from the intratumoral and peri-tumoral regions. In one embodiment, radiomic features from the intra-tumoral and peri-tumoral compartments are extracted from pre-treatment CT scans. FIG. 2 illustrates a CT image of a region of tissue including an invasive GGO nodule at 210, with a magnified region illustrated at 212. FIG. 2 further illustrates a region of tissue including a minimally invasive GGO nodule at 220, with a magnified region illustrated at 222. In this example, thirteen Haralick features capturing textural patterns and which are predictive of variation in tumor micro-architecture, heterogeneity and local appearance of nodules are extracted. Thirteen co-occurrence of local anisotropy gradients (CoLIAGe) features that capture textural entropy structural disorder by applying gray level co-occurrence matrix (GLOM) metrics of disorder to local dominant intensity gradients, are also extracted. FIG. 3 illustrates, at 310, an intra-tumoral CoLIAGe feature extracted from the invasive GGO nodule. FIG. 3 also illustrates, at 320, a peri-tumoral CoLIAGe feature extracted from a 0-3 mm annular ring of the invasive GGO nodule. FIG. 3 illustrates, at 340, an intra-tumoral CoLIAGe feature extracted from the minimally invasive GGO nodule. FIG. 3 also illustrates, at 350, a peri-tumoral CoLIAGe feature extracted from a 0-3 mm annular ring of the minimally invasive GGO nodule. In addition to textural features, in this example, 25 Laws, 25 Laplace, and 48 Gabor features from the intra-tumoral and peri-tumoral regions are also extracted. Laws features and Laplace features are filter-based descriptors that capture textural patterns. Gabor features capture different spatial frequencies within the image at directional orientations. First-order statistics, including, for example, mean, median, standard deviation, skewness, and kurtosis, of each feature are computed across all the pixels, or a threshold number of pixels, and the three slices containing the largest tumor area per patient, respectively.

Embodiments extract radiomic peri-tumoral features from medical imagery, including CT imagery, in an annular ring shaped fashion. In one embodiment, five peri-tumoral annular rings are analyzed, each with a 3 mm increment leading up to a maximum radius of 15 mm from the nodule boundary. In another embodiment, other increments, maximum radii, or number of annular rings may be employed. In one embodiment, the peri-tumoral volume is defined by performing a morphological dilation of the tumoral boundary. A peri-tumoral region may be defined as the region surrounding the tumoral region out to a distance (e.g., maximum radius). For example, in one embodiment, the peri-tumoral region may be the region extending 20 mm from the tumoral boundary, or 100 pixels from the tumoral boundary. In another embodiment, the peri-tumoral region may be the region extending 10 mm, or 50 pixels from the tumoral boundary. The peri-tumoral region may be defined by a distance measured in mm, as described, or in other units, including pixels or voxels. In one embodiment, the peri-tumoral boundary may be defined as a function of a property of the tumor. The property of the tumor may include, for example, a diameter, a radius, a perimeter, an area, a volume, or other property of the tumor. The function may define the peri-tumoral region as, for example, a morphologic dilation of the tumoral boundary, where the dilation ratio is defined by a magnitude of an axis of the tumor. In another embodiment, the peri-tumoral boundary may be defined as a disc of a threshold radius defined about the centroid of the tumor, or defined on the focal points of an elliptical representation of the tumor. In one embodiment, the peri-tumoral boundary may be manually defined. Other approaches or combinations of approaches may be used to define the peri-tumoral boundary. Defining the peri-tumoral volume includes acquiring electronic data, reading from a computer file, receiving a computer file, reading from a computer memory, or other computerized activity not practically performed in a human mind.

Figure 6A:
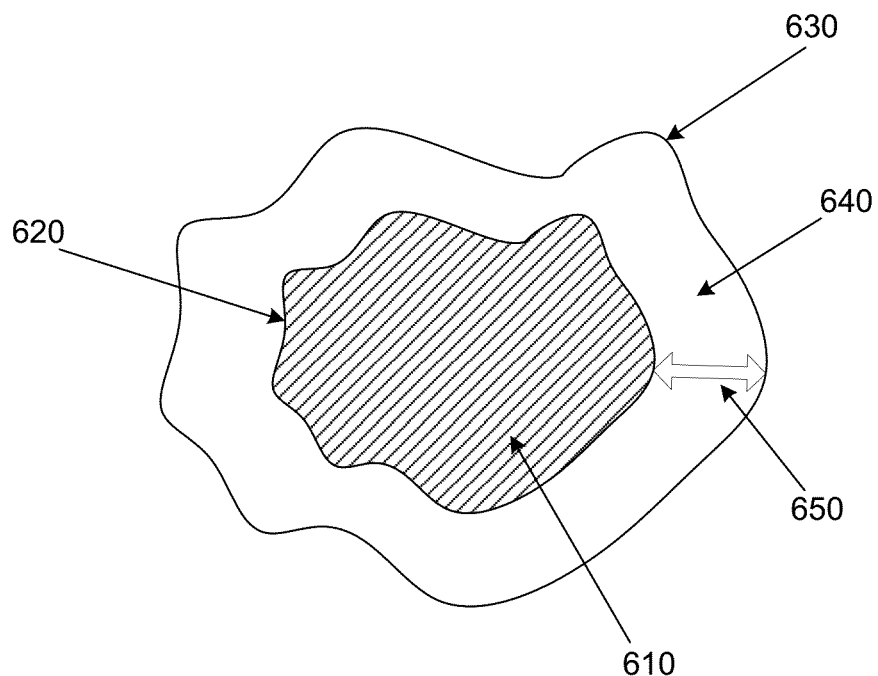
FIGS. 6A-6B illustrate exemplary tumoral and peri-tumoral regions.
Figure 6B:
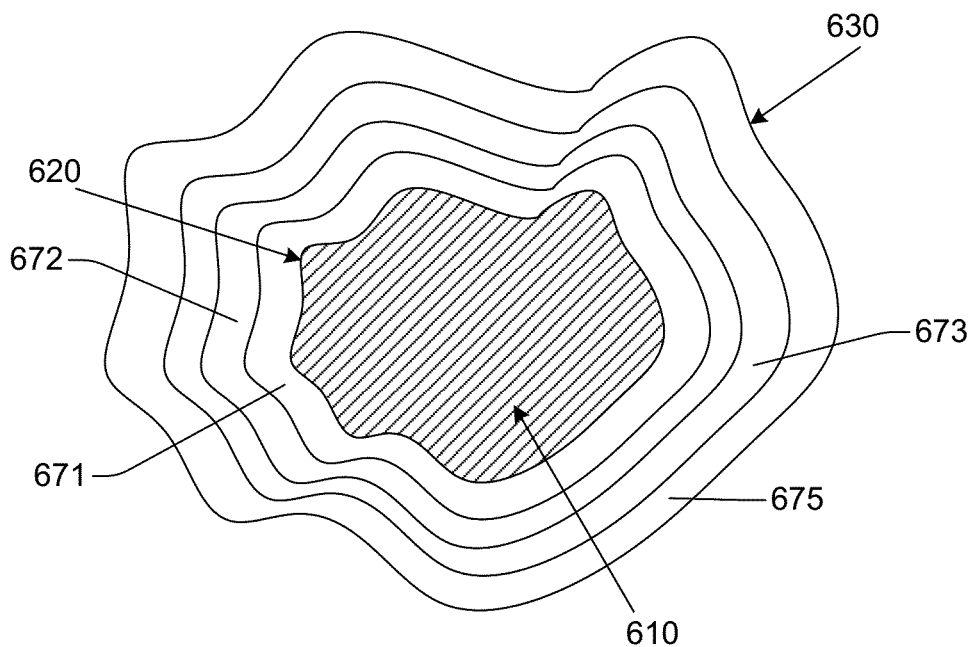

FIG. 6A illustrates an example tumoral region 610. Tumoral region 610 has a boundary 620. A peri-tumoral region 640 is defined by dilating the boundary 620 a first amount 650 (e.g., 20 pixels), generating a peri-tumoral boundary 630. FIG. 6B illustrates annular rings 671, 672, 673, and 675.

Figure 12:
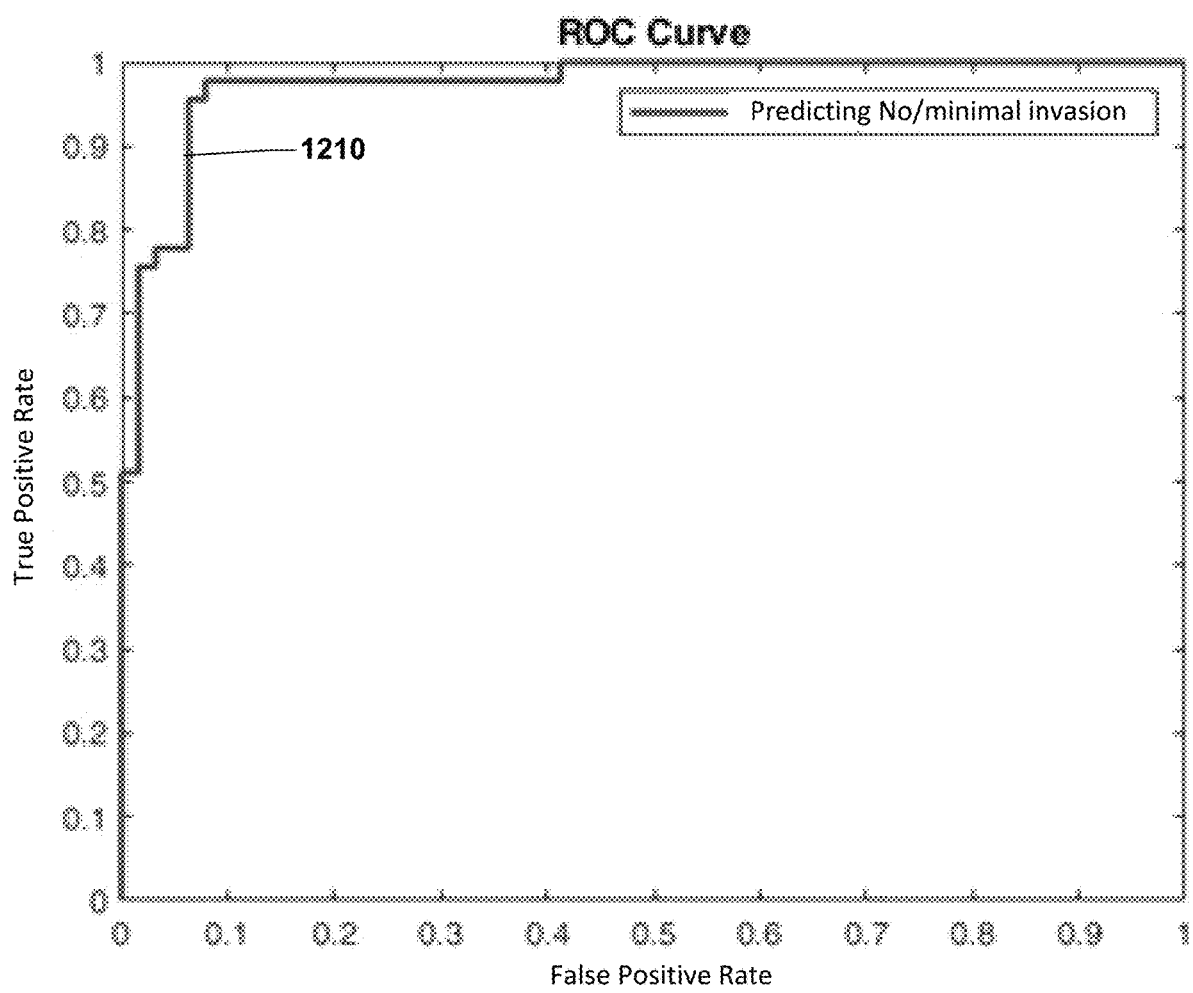
FIG. 12 illustrates an intra-class correlation coefficient (ICC) curve for radiomic features according to embodiments.

Embodiments select a set of discriminative features from among the radiomic features extracted from the tumoral and peri-tumoral regions. Selecting the set of discriminative features may include analyzing the stability and reproducibility of a feature, and generating a set of stable and reproducible features. Feature stability and reproducibility may be evaluated using the Reference Imaging Database to Evaluate Response (RIDER) test-retest dataset. The RIDER test-retest dataset contains data and imagery of 31 lung cancer patients, scanned two times each, fifteen minutes apart. Two scans of every patient in the RIDER test-retest dataset were used for calculating an intra class correlation coefficient (ICC). Radiomic features were extracted from two scans of the same patients. These radiomic features were compared against each other to calculate an ICC. ICC measures similarity between two feature vectors. Employing a threshold of 0.8, all feature vectors having value less than this threshold were removed from analysis. A total of 4464 features were reduced to 744 after applying stable feature conditions. In another embodiment, another, different threshold may be employed (e.g., 0.7, 0.9). FIG. 12 illustrates the ICC curve 1210 for radiomic features according to embodiments based on the RIDER test-retest dataset.

Embodiments may further select the top most discriminative features from among the stable and reproducible features using a feature selection technique. In one embodiment, a minimum redundancy maximum relevance (mRMR) feature selection technique is employed to select the top five most discriminative features that discriminate frank invasive nodules from MIA or AIS nodules. MRMR feature selection identifies a set of features that maximally distinguish two classes while minimizing intra-feature correlation. The mRMR feature selection technique is, in this example, implemented across two-hundred iterations of three-fold cross-validation within the training cohort. In this example, the number of features selected is capped at five, to prevent overfitting due to the curse of dimensionality arising from an overabundance of features relative to the sample size. Embodiments may analyze the top radiomic feature set using box-and-whisker plots and qualitative feature maps comparing feature expressions between MIA/AIS and invasive adenocarcinomas. In another embodiment, the top N most discriminative features may be selected, N being an integer. In another embodiment, other numbers of iterations of cross-validation may be employed.

Embodiments may validate the ability of a radiomic feature set that includes intratumoral and peri-tumoral features to distinguish MIA and AIS from invasive adenocarcinoma using different types of machine learning classifiers. In one example, five different machine learning classifiers are evaluated to verify that prediction was driven by the selected features as opposed to the choice of classifier. The following classifiers were explored: linear discriminant analysis (LDA), diagonal linear discriminant analysis (DLDA), quadratic discriminant analysis (ODA), diagonal quadratic discriminant analysis (MLA) and support vector machine (SVM). Performance was assessed by area under the receive operating characteristic curve (AUC), accuracy, sensitivity (i.e., the ability to identify patients who had invasive component), and specificity (i.e., the ability to correctly identify patients who had frank invasion).

Of the 147 nodules, 54 nodules were pathologically confirmed as pre-invasive lesions (AIS, n=7), minimally-invasive lesions (MIA, n=47), whereas 93 were confirmed as invasive lesions. All invasive patients, in this example, were stage 1A cases, with invasive lesions having a diameter of less than 2 cms.

In one embodiment, the top five most discriminative selected stable features included four from inside the tumor (2 Haralick features, 1 Gabor, 1 Collage) and one from immediately outside the tumor (1 Collage) (0-3 mm) which successfully differentiated INV from MIA and AIS with an AUC of 0.97 (p<0.05) (sensitivity—95.5%, specificity—94%). In this example, textural features from within the nodule that quantify tumor heterogeneity were found to be the most predictive followed by peri-tumoral features from an annular ring extending from the tumor boundary to 3 mm outside the tumor.

Figure 11:
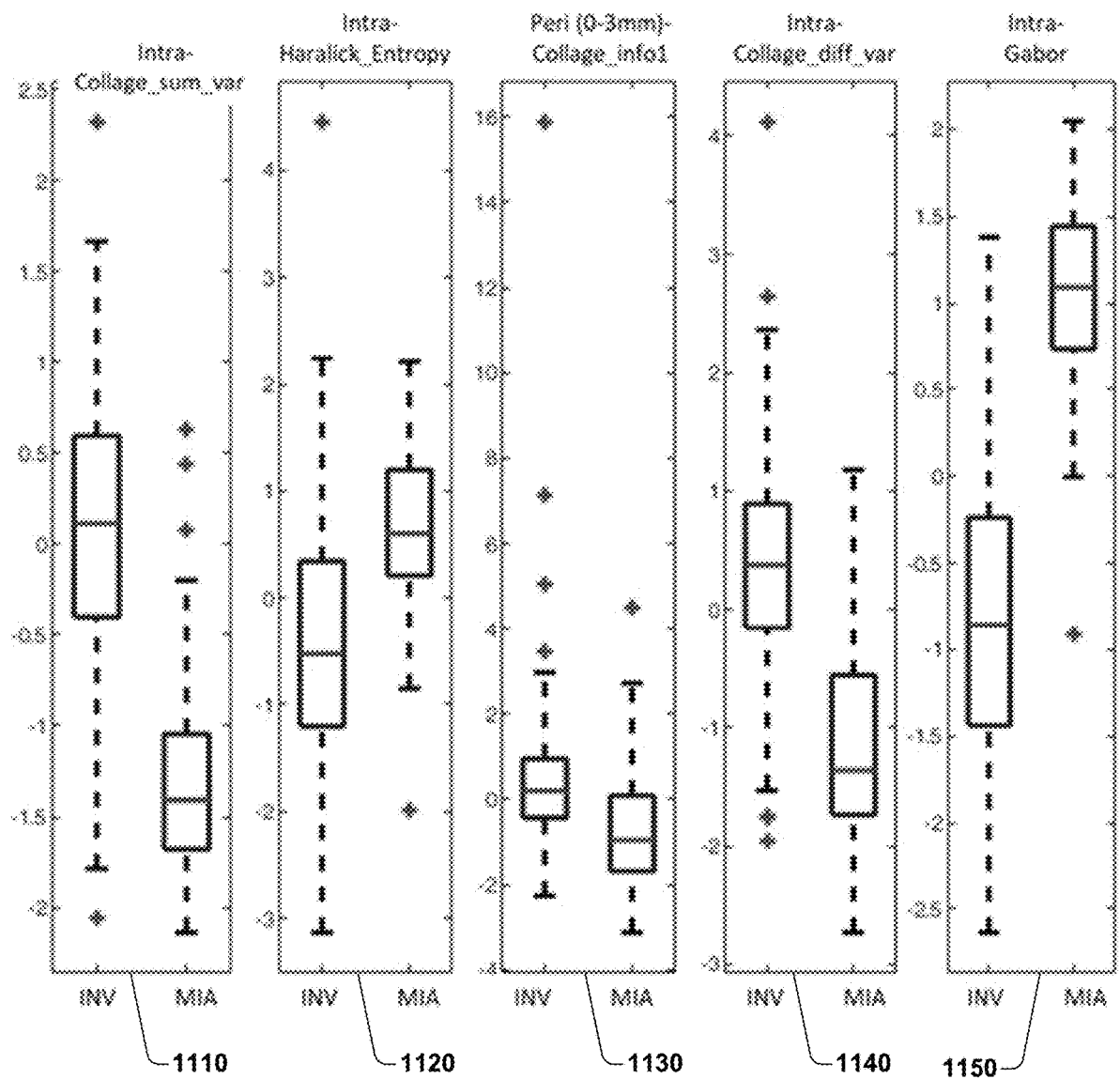
FIG. 11 illustrates box and whisker plots of radiomic features for distinguishing AIS and MIA from invasive adenocarcinoma.

FIG. 11 illustrates box and whisker plots 1110, 1120, 1130, 1140, and 1150 that correspond to the top five most discriminative radiomic features obtained during feature discovery. Boxplots 1110-1150 indicate features that show elevated expression amongst invasive adenocarcinoma cases compared with MIA/AIS in both the training and testing sets. Four features from inside the nodule included 2 Haralick, 1 Gabor and 1 CoLIAGe feature. The 5th feature was a CoLIAGe feature from 0-3 mm outside the tumor region. In this example, the top five most discriminative features includes a standard deviation of an intratumoral CoLIAGe sum-variance feature, a skewness of an intratumoral Haralick entropy feature, a mean of a peri-tumoral CoLIAGe information 1 feature extracted from a the 0-3 mm annular ring, a standard deviation of a an intratumoral CoLIAGe difference variation feature, and a mean of an intraturmoral Gabor feature. In other embodiments, the top five most discriminative features may include other, different features. In other embodiments, other statistics of the discriminative features may be computed or employed in distinguishing invasive adenocarcinoma from MIA/AIS.

The skewness of intratumoral initial Laws spot-ripple feature, and standard deviation (SD) of a Laplace level-spot feature, demonstrate that MIA/AIS and frank invasive tumors differed in patterns of enhancement textures. The fifth top feature, kurtosis of peri-tumoral collage sum entropy, was expressed more strongly within the peri-tumoral region of frank invasive patients.

Embodiments may train a machine learning classifier to distinguish MIA/AIS nodules from invasive adenocarcinoma. In one embodiment, the optimal classifier performance within the training set was achieved using an LDA classifier trained with the top five most discriminative features across one-hundred threefold cross-validation iterations, yielding an average AUC of 0.97±0.02 and accuracy of (0.95±0.03). Within the testing set, an LDA classifier had an AUC of 0.97, sensitivity of 95.5%, and specificity of 94%. In another embodiment, a DLDA classifier distinguishes MIA/AIS from invasive adenocarcinoma with an AUC of 0.93. In another embodiment, a ODA classifier distinguishes MIA/AIS from invasive adenocarcinoma with an AUC of 0.86. In another embodiment, an SVM classifier distinguishes MIA/AIS from invasive adenocarcinoma with an AUC of 0.89. Embodiments thus provide the technical effect of providing improved accuracy in systems, apparatus, processors, computers, or other implementations that distinguish MIN/AIS from invasive adenocarcinoma in CT images of tissue demonstrating cancerous pathology. Various embodiments can provide features and advantages not available in existing systems. Embodiments facilitate distinguishing frank invasive adenocarcinoma from minimally invasive adenocarcinoma and adenocarcinoma in situ in a non-invasive way, and with greater accuracy than existing approaches, and may be further employed as a clinical decision support tool for treatment planning based on diagnostic CT imagery of lung tissue.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 4:
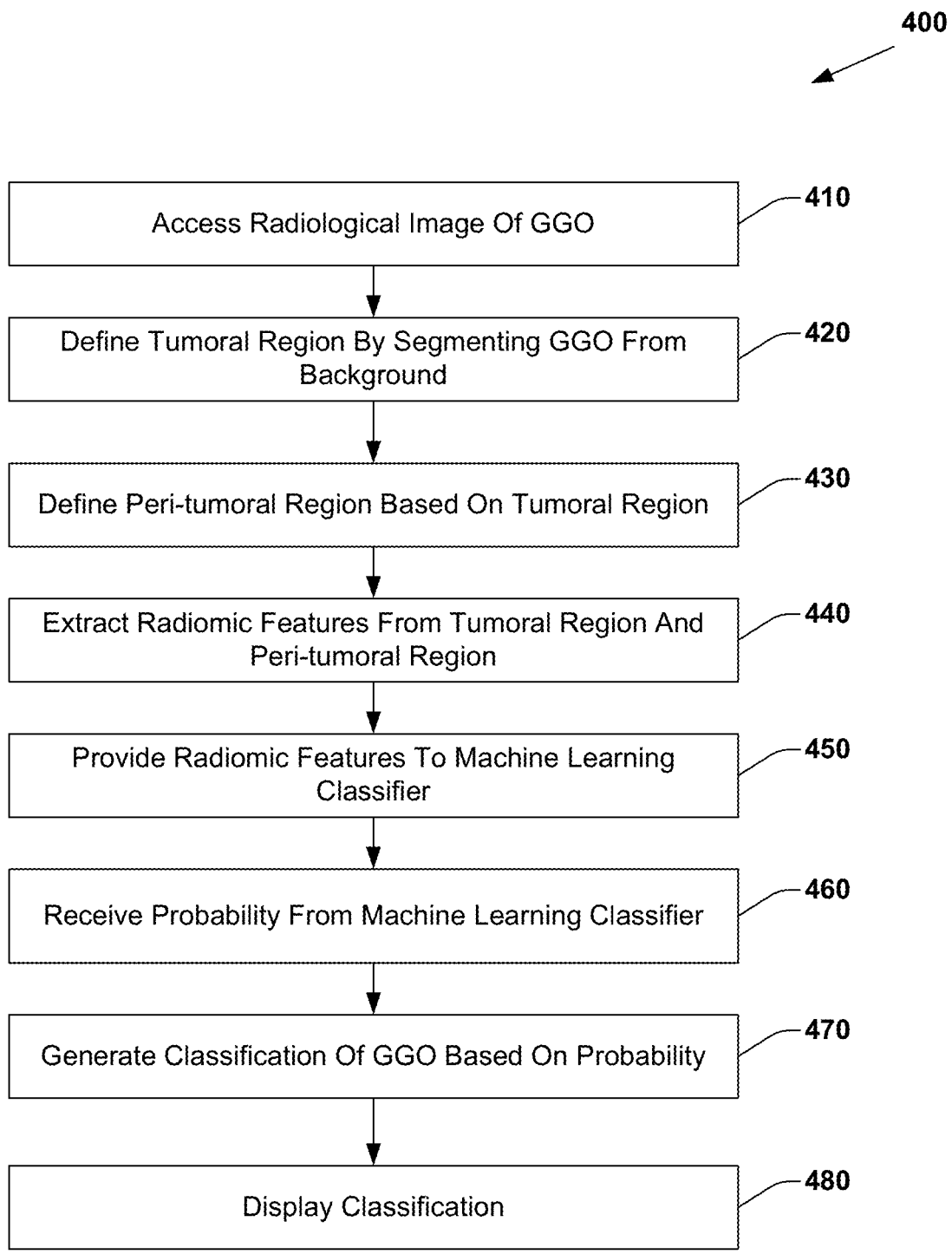
FIG. 4 is a flow diagram of example operations for distinguishing adenocarcinoma in situ (AIS) and MIA from invasive adenocarcinoma.

FIG. 4 is a flow diagram of example operations 400 that may be performed by a processor for distinguishing MIA/AIS from invasive adenocarcinoma represented in medical imagery. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations or methods described herein. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 400 includes, at 410, accessing an image of a region of tissue. The region of tissue includes lung tissue. The image may be a digitized medical image of a region of tissue demonstrating lung nodules. The region of tissue includes a nodular region, including, for example a GGO nodule. Accessing the image includes acquiring electronic data, reading from a computer file, receiving a computer file, reading from a computer memory, or other computerized activity not practically performed in the human mind. A member of the set of images has a plurality of pixels, a pixel having an intensity. In one embodiment, the image is a non-contrast computed tomography (CT) image of a region of tissue demonstrating lung nodules. The image may have a plurality of slices. A slice has a slice thickness. The slice thickness may be in the range [1 mm, 5 mm]. The CT image parameters may include slice thickness, image resolution in the x, y, or z plane, sequence, reconstruction kernels, contrast enhancements, or contrast intensity. In another embodiment, the image may be acquired using other, different imaging parameters, or different values of the imaging parameters. In one embodiment, images acquired from a first institution or from a first CT system may have different imaging parameters or imaging parameter values than images acquired from a second, different institution or second, different CT system. Accessing the image includes acquiring electronic data, reading from a computer file, receiving a computer file, reading from a computer memory, or other computerized activity not practicably performed in the human mind.

The set of operations 400 also includes, at 420 defining a tumoral region by segmenting the GGO nodule, where defining the tumoral region includes defining a tumoral boundary. In one embodiment, the tumoral region has a diameter less than or equal to two centimeters. Defining the tumoral region may include segmenting a tumoral region represented in the image. Segmenting the tumoral region includes defining a tumoral boundary. In one embodiment, segmenting a tumoral region represented in the image includes segmenting the tumoral region using a watershed segmentation technique. The watershed segmentation technique includes applying, at a plurality of scales, a fast radial symmetry transform and regional minima to the image. A scale may be, for example 5×, 10× or 20×. In another embodiment, another, different automated segmentation technique may be employed. For example, a deep learning based neural network may be employed to delineate the tumoral boundary based on a large number of training exemplars. In another embodiment, the tumoral region and tumoral boundary are already segmented and thus, in one embodiment, operation 420 may be skipped. Segmenting the tumoral region includes acquiring electronic data, reading from a computer file, receiving a computer file, reading from a computer memory, or other computerized activity not practicably performed in the human mind.

The set of operations 400 also includes, at 430, defining a peri-tumoral region based on the tumoral boundary. In one embodiment, the peri-tumoral region is defined by performing a dilation of the tumoral boundary. The peri-tumoral region may include a plurality of annular rings. For example, the tumoral boundary may be dilated 15 mm to generate a peri-tumoral boundary, and the peri-tumoral region may be divided into 5 annular rings having an interval of 3 mm each. FIG. 6B illustrates a tumoral region 610 having a tumoral boundary 620 and a peri-tumoral boundary 630. The peri-tumoral region is the region between the tumoral boundary 620 and the peri-tumoral boundary 630. In the example illustrated in FIG. 6B, the peri-tumoral region includes four annular rings 671, 672, 673, and 675. In another embodiment, the peri-tumoral region may be defined based on a function of a property of the tumoral region. Defining the peri-tumoral region includes acquiring electronic data, reading from a computer file, receiving a computer file, reading from a computer memory, or other computerized activity not practicably performed in the human mind.

The set of operations 400 also includes, at 440, extracting a set of radiomic features from the peri-tumoral region and the tumoral region. In one embodiment, the set of radiomic features includes at least five radiomic features. In one embodiment, the at least five radiomic features includes four tumoral radiomic features, and one peri-tumoral radiomic feature. In one embodiment, the set of radiomic features includes: a tumoral co-occurrence of local anisotropy gradients (CoLlAGe) feature; a first tumoral Haralick feature; a second, different tumoral Haralick feature; a tumoral Gabor feature; and a peri-tumoral CoLlAGe feature. In one embodiment, the peri-tumoral CoLlAGe feature is extracted from a first annular ring extending from the tumoral boundary to 3 mm from the tumoral boundary. In another embodiment, other, different radiomic features may be extracted. Extracting the set of radiomic features includes acquiring electronic data, reading from a computer file, receiving a computer file, reading from a computer memory, or other computerized activity not practicably performed in the human mind.

The set of operations 400 also includes, at 450, providing the set of radiomic features to a machine learning classifier trained to distinguish minimally invasive adenocarcinoma (MIA) and adenocarcinoma in situ (AIS) from invasive adenocarcinoma. In one embodiment, the machine learning classifier is a linear discriminant analysis (LDA) classifier. In this embodiment, the LDA classifier computes the probability with an area under the receiver operating curve (AUC) of at least 0.97, a sensitivity of at least 95.5%, and a specificity of at least 94%. In another embodiment, the machine learning classifier is a diagonal LDA (DLDA) classifier, a quadratic discriminant analysis (QDA) classifier, a support vector machine (SVM) classifier, or other machine learning or deep learning classifier trained to distinguish a positive class from a negative class. Providing the set of radiomic features to the machine learning classifier includes acquiring electronic data, reading from a computer file, receiving a computer file, reading from a computer memory, or other computerized activity not practicably performed in the human mind.

The set of operations 400 also includes, at 460, receiving, from the machine learning classifier, a probability that the GGO nodule is invasive adenocarcinoma. The machine learning classifier computes the probability based on the set of radiomic features. Receiving the probability from the machine learning classifier includes acquiring electronic data, reading from a computer file, receiving a computer file, reading from a computer memory, or other computerized activity not practicably performed in the human mind.

The set of operations 400 also includes, at 470, generating a classification of the GGO nodule as MIA or AIS, or invasive adenocarcinoma, based, at least in part, on the probability. For example, a probability of [1, 0.5] may result in a classification of the GGO nodule as invasive adenocarcinoma, while a probability of (0.5, 0] may result in a classification of the GGO nodule as MIA or AIS. Other classification schemes may be employed. For example, in one embodiment, the GGO nodule may be classified according to a scheme of "MAI/AIS, unknown, invasive adenocarcinoma". Generating the classification includes acquiring electronic data, reading from a computer file, receiving a computer file, reading from a computer memory, or other computerized activity not practicably performed in the human mind.

The set of operations 400 further includes, at 480, displaying the classification. Displaying the classification may include displaying the classification on a computer monitor, a smartphone display, a tablet display, or other displays. Displaying the classification may also include printing the classification. Displaying the classification may also include controlling a lung nodule classification system, a CADx system, a monitor, or other display, to display operating parameters or characteristics of a machine learning classifier, during both training and testing, or during clinical operation of the machine learning classifier. By displaying the classification or operating parameters or characteristics of the machine learning classifier, example embodiments provide a timely and intuitive way for classifying lung nodules, including lung nodules in NSCLC, thus improving on existing approaches to classification of lung nodules.

Embodiments may further display the GGO nodule, the tumoral region, the tumoral boundary, the peri-tumoral region, an annular ring, the set of radiomic features, or the probability. Displaying the classification includes acquiring electronic data, reading from a computer file, receiving a computer file, reading from a computer memory, or other computerized activity not practicably performed in the human mind.

Figure 5:
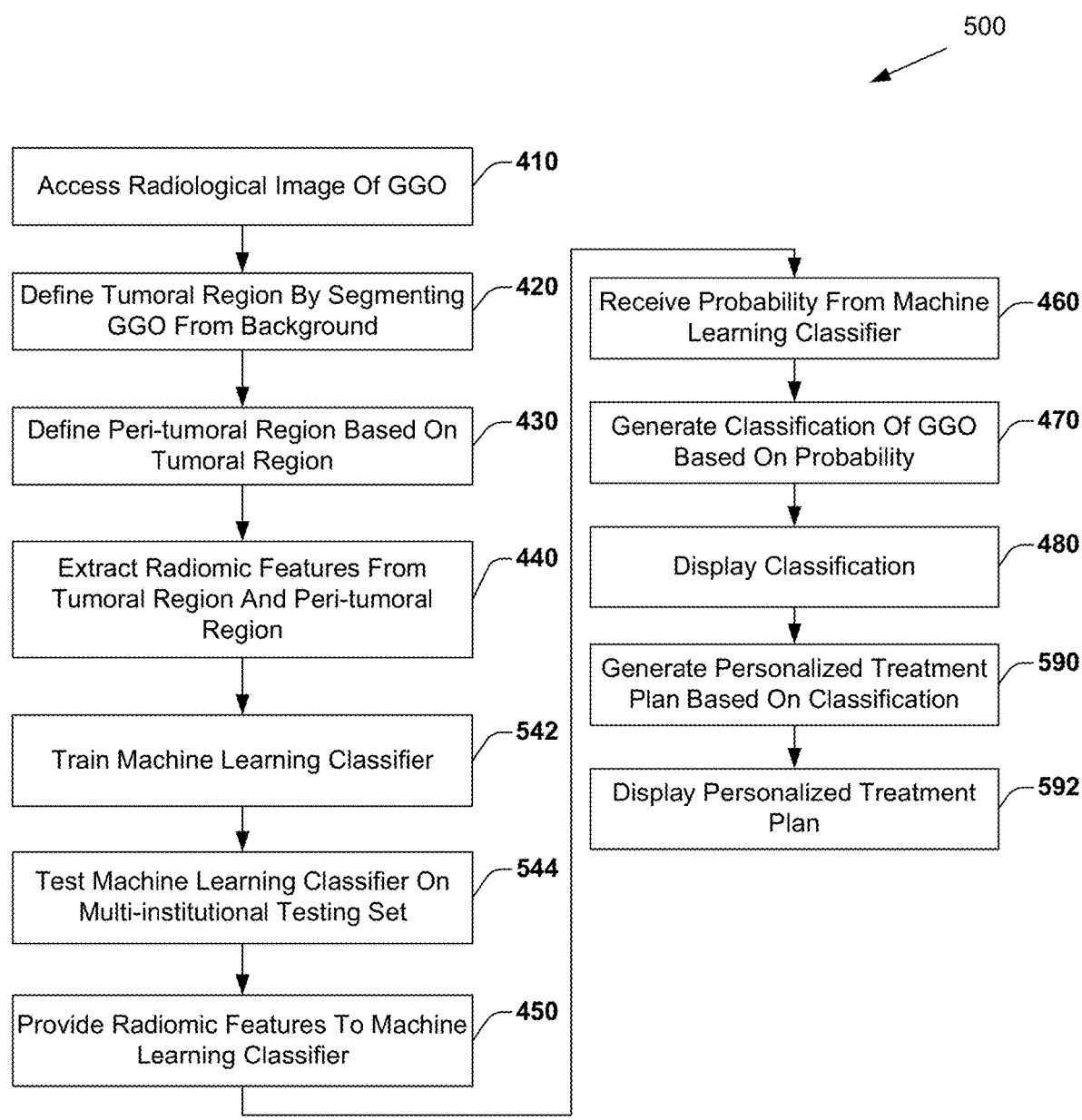
FIG. 5 is a flow diagram of example operations for distinguishing AIS and MIA from invasive adenocarcinoma.

FIG. 5 illustrates a set of operations 500 that is similar to operations 400 but that includes additional elements and details. In one embodiment, operations 500 includes, at 542, training the machine learning classifier. In this embodiment, the machine learning classifier is trained and tested using a training set of images and a testing set of images. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining which radiomic features are most discriminative in distinguishing MIA or AIS tissue from invasive adenocarcinoma, or determining the optimal combination of parameters used in the computation of the probability (e.g., maximum peri-tumoral radius to include, or size and number of annular subregions analyzed) to best separate a positive and negative class. In this embodiment, operations 500 also includes, at 544, testing the machine learning classifier on a multi-institutional testing cohort. Testing the machine learning classifier on a multi-institutional testing cohort provides the technical effect of validating the model for different imaging parameters. Different institutions may have different scanners or scanning parameters. Multi-institutional validation confirms that the model employed by embodiments is robust and that external parameters or noise would not affect the output variable. In existing approaches that train and validate on the same institutional cohort, there is a possibility of overfitting which is substantially reduced when the classifier is validated on different institutional validation sets.

In one embodiment, operations 500 also includes, at 590, generating a personalized treatment plan. The personalized treatment plan is based, at least in part, on the classification. In one embodiment, the personalized treatment plan is further based on the image or the probability. Generating a personalized treatment plan facilitates delivering a particular treatment that will be therapeutically active to the patient, while minimizing negative or adverse effects experienced by the patient. For example, the personalized treatment plan may suggest a surgical treatment, may define an immunotherapy agent dosage or schedule, or a chemotherapy agent dosage or schedule, when the region of tissue is classified as invasive adenocarcinoma. For a region of tissue classified as MIA or AIS, other treatments may be suggested. In this embodiment, operations 500 further includes, at 592 displaying the personalized treatment plan.

While FIGS. 4 and 5 illustrate various actions occurring in serial, it is to be appreciated that various actions illustrated in FIG. 4 or 5 could occur substantially in parallel. By way of illustration, a first process could involve extract set of radiomic features, a second process could involve providing the set of radiomic features to a machine learning classifier, and a third process could involve classifying a region of tissue. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including methods or operations 400, 500, or 900. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Improved classification of lung nodules, including classification as MIA/AIS or invasive adenocarcinoma, may produce the technical effect of improving treatment efficacy by increasing the accuracy of and decreasing the time required to treat patients demonstrating lung nodules, or other forms of cancerous pathology. Treatments and resources, including expensive immunotherapy agents or chemotherapy may be more accurately tailored to patients with a likelihood of benefiting from said treatments and resources, including responding to immunotherapy or chemotherapy, so that more appropriate treatment protocols may be employed, and expensive resources are not wasted. Controlling a personalized medicine system, a computer assisted diagnosis (CADx) system, a processor, or lung nodule classification system or apparatus based on improved, more accurate identification or classification of tissue further improves the operation of the system, processor, or apparatus, since the accuracy of the system, processor, or apparatus is increased and unnecessary operations will not be performed. Embodiments described herein, including at least the sets of operations 400 and 500, apparatus 700 and 800, and method 900, resolve features extracted from medical imagery, including CT images, at a higher order or higher level than a human can resolve in the human mind or with pencil and paper. For example, the standard deviation of a CoLlAGe sum variance feature is not a biological property of cancerous tissue that a human eye can perceive. A tumor does not include a set of annular rings defined by a function of a property of a tumor, and these features cannot be stored in a human mind. The human mind is not equipped to detect statistical properties of radiomic features using digitized medical imagery stored in a computer memory and analyzing a set of radiomic features using machine learning techniques as described herein. Embodiments described herein use a combined order of specific rules, elements, operations, or components that render information into a specific format that is then used and applied to create desired results more accurately, more consistently, and with greater reliability than existing approaches, thereby producing the technical effect of improving the performance of the machine, computer, or system with which embodiments are implemented.

Using a more appropriately modulated treatment may lead to less aggressive therapeutics being required for a patient or may lead to avoiding or delaying a biopsy, a resection, or other invasive procedure. When patients demonstrating invasive adenocarcinoma are more accurately distinguished from patients who demonstrate MIA or AIS, patients most at risk may receive a higher proportion of scarce resources (e.g., therapeutics, physician time and attention, hospital beds) while those less likely to benefit from the treatment, or less in need, may be spared unnecessary treatment, which in turn spares unnecessary expenditures and resource consumption. Example methods, apparatus, and other embodiments may thus have the additional effect of improving patient outcomes compared to existing approaches.

Figure 7:
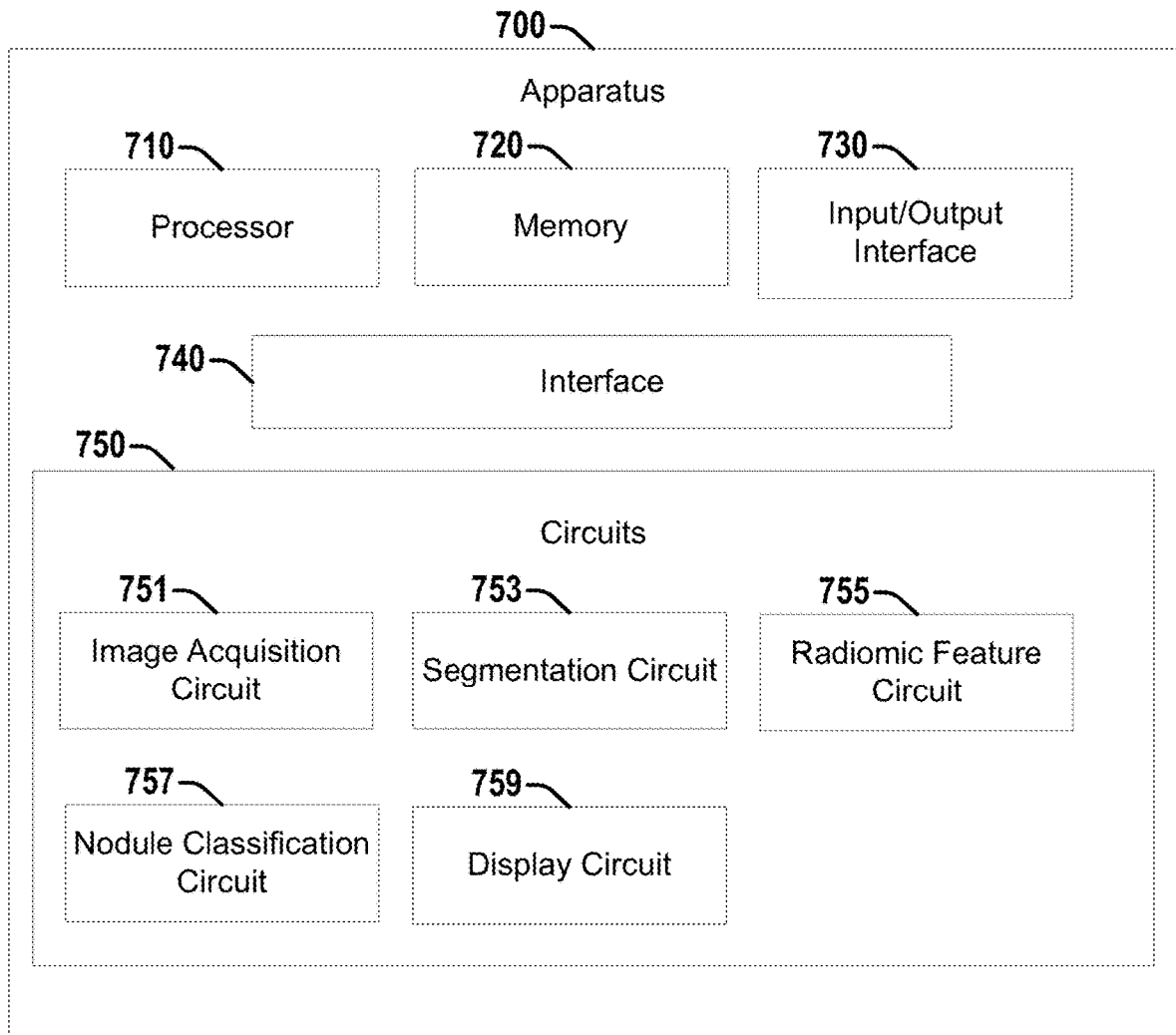
FIG. 7 illustrates an example apparatus for distinguishing AIS and MIA from invasive adenocarcinoma.

FIG. 7 illustrates an example apparatus 700. Apparatus 700 may be configured to distinguish MIA and AIS nodules from invasive adenocarcinoma. Apparatus 700 includes a processor 710. Apparatus 700 also includes a memory 720. Processor 710 may, in one embodiment, include circuitry such as, but not limited to, one or more single-core or multi-core processors. Processor 710 may include any combination of general-purpose processors and dedicated processors (e.g., graphics processors, application processors, etc.). The processors may be coupled with or may include memory (e.g. memory 720) or storage and may be configured to execute instructions stored in the memory or storage to enable various apparatus, applications, or operating systems to perform the operations. Memory 720 is configured to store a digitized medical image, including a digitized CT image of a region of tissue demonstrating lung nodules. The digitized image has a plurality of pixels, a pixel having an intensity. Memory 720 may be further configured to store a training set of CT images of tissue demonstrating lung nodules, or a testing set of CT images demonstrating lung nodules. In another embodiment, memory 720 may be configured to store medical imagery of tissue demonstrating lung nodules acquired using other, different imaging modalities, include, for example, magnetic resonance imaging (MRI).

Apparatus 700 also includes an input/output (I/O) interface 730, a set of circuits 750, and an interface 740 that connects the processor 710, the memory 720, the I/O interface 730, and the set of circuits 750. I/O interface 730 may be configured to transfer data between memory 720, processor 710, circuits 750, and external devices, for example, a computer assisted diagnostic (CADx) system or a personalized medicine system.

The set of circuits 750 includes an image acquisition circuit 751, a segmentation circuit 753, a radiomic feature circuit 755, a nodule classification circuit 757, and a display circuit 759.

Image acquisition circuit 751 is configured to access a diagnostic image of a region of tissue including a GGO nodule. Accessing the diagnostic image may include accessing a digitized CT image of a region of tissue demonstrating lung nodules (e.g., GGO nodule), stored in memory 720. The diagnostic image has a plurality of pixels, a pixel having an intensity. The diagnostic image may have a plurality of slices, a slice having a thickness. In another embodiment, the diagnostic image may be an MRI image, or other type of radiological or medical image. Accessing the diagnostic image includes acquiring electronic data, reading from a computer file, receiving a computer file, reading from a computer memory, or other computerized activity that cannot practically be performed in the human mind.

Segmentation circuit 753 is configured to define a tumoral region by segmenting the GGO nodule. Segmentation circuit 753 is configured to segment the GGO nodule by defining a tumoral boundary. Segmentation circuit 753 is also configured to define a peri-tumoral region based on a dilation of the tumoral boundary. In another embodiment, segmentation circuit 753 is configured to define the peri-tumoral region using a function of a property of the tumoral region.

Radiomic feature circuit 755 is configured to extract a set of radiomic features from the peri-tumoral region and the tumoral region. In one embodiment, the set of radiomic features includes: a tumoral co-occurrence of local anisotropy gradients (CoLIAGe) feature; a first tumoral Haralick feature; a second, different tumoral Haralick feature; a tumoral Gabor feature; and a peri-tumoral CoLIAGe feature. In another embodiment, the set of radiomic features may include another, different number of features, or other, different features. Radiomic feature circuit 755 is configured to compute first order statistics of the members of the set of radiomic features.

Nodule classification circuit 757 is configured to compute a probability that the GGO nodule is invasive adenocarcinoma based on the set of radiomic features. Nodule classification circuit 757 is also configured to generate a classification of the GGO nodule as minimally invasive adenocarcinoma (MIA) or adenocarcinoma in situ (AIS), or invasive adenocarcinoma, based, at least in part, on the probability. In one embodiment, nodule classification circuit 757 is configured to compute the probability that the GGO nodule is invasive adenocarcinoma using a linear discriminant analysis (LDA) machine learning approach. In another embodiment, nodule classification circuit 757 may be configured to compute the probability that the GGO nodule is invasive adenocarcinoma using a different machine learning approach. Nodule classification circuit 757 may be configured to compute the probability that the GGO nodule is invasive adenocarcinoma based on first order statistics associated with the members of the set of radiomic features.

In one embodiment, nodule classification circuit 757 includes a machine learning classifier configured to compute the probability based, at least in part, on the set of radiomic features. The machine learning classifier may employ a linear discriminant analysis (LDA) classification approach. In this embodiment, the machine learning classifier is trained on a set of training images. In one embodiment, a member of the set of training images is acquired using different imaging parameters than the diagnostic image. In another embodiment, nodule classification circuit 757 may be configured as another type of machine learning or deep learning classifier, including as an DLDA classifier, a QDA classifier, an SVM classifier, or a CNN classifier.

Display circuit 759 is configured to display the classification. In one embodiment, display circuit 759 is configured to display the classification, the probability, the personalized treatment plan, the set of radiomic features, or the diagnostic image on a computer monitor, a smartphone display, a tablet display, or other displays. Displaying the classification, the probability, a personalized treatment plan, the set of radiomic features, or the diagnostic image may also include printing the classification, the probability, a personalized treatment plan, the set of radiomic features, or the diagnostic image. Display circuit 759 may also control a CADx system, a monitor, or other display, to display operating parameters or characteristics of image acquisition circuit 751, segmentation circuit 753, radiomic feature circuit 755, or nodule classification circuit 757, including a machine learning classifier, during both training and testing, or during clinical operation of apparatus 700 or apparatus 800.

Figure 8:
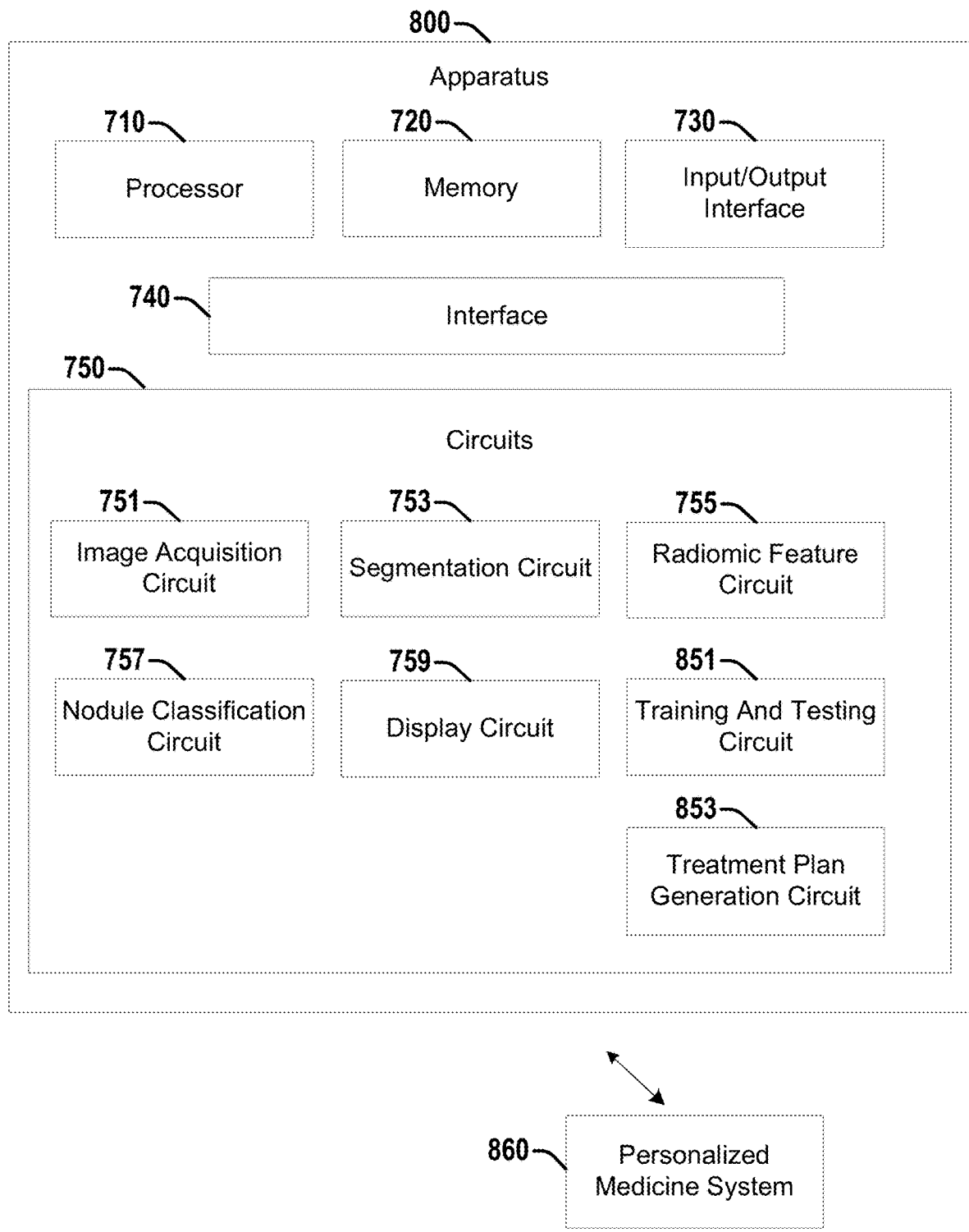
FIG. 8 illustrates an example apparatus for distinguishing AIS and MIA from invasive adenocarcinoma.

FIG. 8 illustrates an apparatus 800 that is similar to apparatus 700 but that includes additional elements and details. Apparatus 800 includes a treatment plan generation circuit 853. Treatment plan generation circuit 853 is configured to generate a personalized treatment plan based, at least in part, on the classification. In one embodiment, the personalized treatment plan is further based on the diagnostic image, or the set of radiomic features. The personalized treatment plan may suggest a surgical treatment, may define an immunotherapy agent dosage or schedule, or a chemotherapy agent dosage or schedule, when the region of tissue is classified as invasive adenocarcinoma. For a region of tissue classified as MIA or AIS, other treatments, schedules, or dosages may be suggested.

In one embodiment, apparatus 800 also includes training and testing circuit 851. Training and testing circuit 851 is configured to train nodule classification circuit 757 according to techniques described herein. Training and testing circuit 851 is configured to train the nodule classification circuit 757 to compute the probability that the GGO nodule is invasive adenocarcinoma using a set of training images, where a member of the set of training images is acquired using different imaging parameters than the diagnostic image. Training nodule classification circuit 757 may include training a machine learning classifier, including an LDA classifier, a random forest classifier, a DLDA classifier, an SVM classifier, or a QDA classifier, or a CNN. In one embodiment, training and testing circuit 851 is configured to access a training dataset of digitized images of a region of interest demonstrating lung nodules. The training dataset includes images of tissue that were classified as AIS or MIA, and images of tissue that were classified as invasive adenocarcinoma. Training and testing circuit 851 may be further configured to access a testing dataset of digitized images of a region of interest demonstrating lung nodules, where the testing dataset includes images of tissue that are classified as AIS or MIA, and images of tissue that are classified as invasive adenocarcinoma. In this embodiment, the machine learning classifier is trained using the training dataset of images and tested using the testing dataset of images. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed.

FIG. 8 further illustrates a personalized medicine device 860. Apparatus 800 may be configured to transmit the classification, the probability, the personalized treatment plan, the set of radiomic features, or the diagnostic image to the personalized medicine device 860. Personalized medicine device 860 may be, for example, a CADx system, a lung nodule classification apparatus or system, or other type of personalized medicine device that may be used to facilitate the classification of tissue. In one embodiment, treatment plan generation circuit 853 may control personalized medicine device 860 to display the classification, the probability, the personalized treatment plan, the set of radiomic features, or the diagnostic image on a computer monitor, a smartphone display, a tablet display, or other displays.

Figure 9:
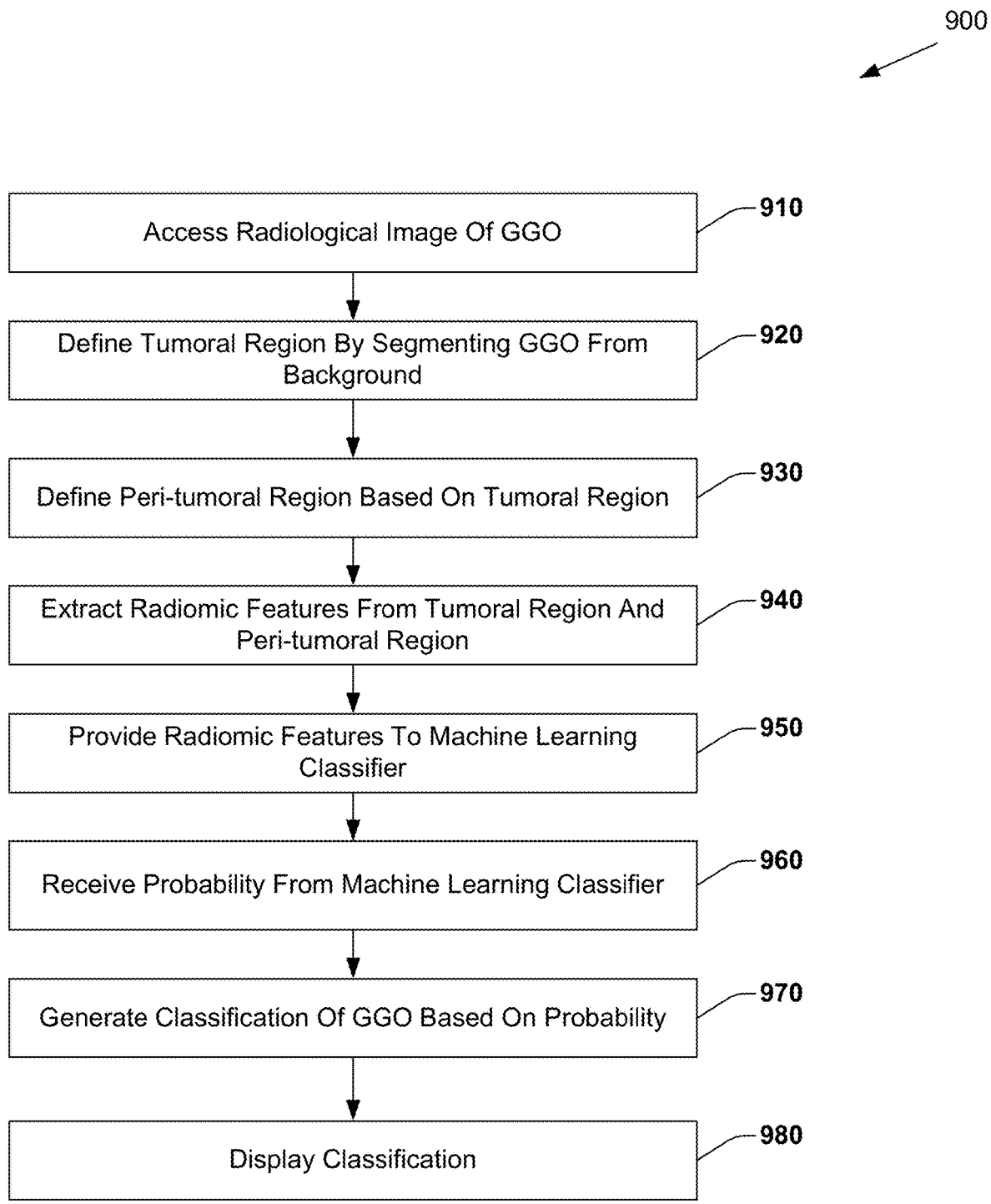
FIG. 9 illustrates an example method for distinguishing AIS and MIA from invasive adenocarcinoma.

FIG. 9 illustrates a method 900. Method 900 includes acquiring electronic data, reading from a computer file, receiving a computer file, reading from a computer memory, or other computerized activity that cannot practically be performed in the human mind. Method 900 includes, at 910, accessing a computed tomography (CT) image of a region of lung tissue, where the CT image includes a ground glass (GGO) nodule, the CT image having a plurality of slices, a slice having a thickness.

Method 900 also includes, at 920, defining a tumoral region by segmenting the GGO nodule. Defining the tumoral region includes defining a tumoral boundary.

Method 900 also includes, at 930, defining a peri-tumoral region based on a morphological dilation of the tumoral boundary. The peri-tumoral region includes at least one annular ring.

Method 900 also includes, at 940, extracting a set of radiomic features from the peri-tumoral region and the tumoral region. The set of radiomic features includes a tumoral co-occurrence of local anisotropy gradients (CoLIAGe) feature, a first tumoral Haralick feature, a second, different tumoral Haralick feature, a tumoral Gabor feature, and a peri-tumoral CoLIAGe feature.

Method 900 also includes, at 950, providing the set of radiomic features to a linear discriminant analysis (LDA) classifier trained to distinguish minimally invasive adenocarcinoma (MIA) and adenocarcinoma in situ (AIS) from invasive adenocarcinoma using a set of training images. A member of the set of training images is acquired using different imaging parameters than the diagnostic image.

Method 900 also includes, at 960, receiving, from the LDA classifier, a probability that the GGO nodule is invasive adenocarcinoma. The machine learning classifier computes the probability based on the set of radiomic features.

Method 900 also includes, at 970, generating a classification of the GGO nodule as MIA or AIS, or invasive adenocarcinoma. The classification is based, at least in part, on the probability.

Method 900 further includes, at 980, displaying the classification. In one embodiment, method 900 also includes, at 980, displaying the probability, the set of radiomic features, or the image.

Figure 10:
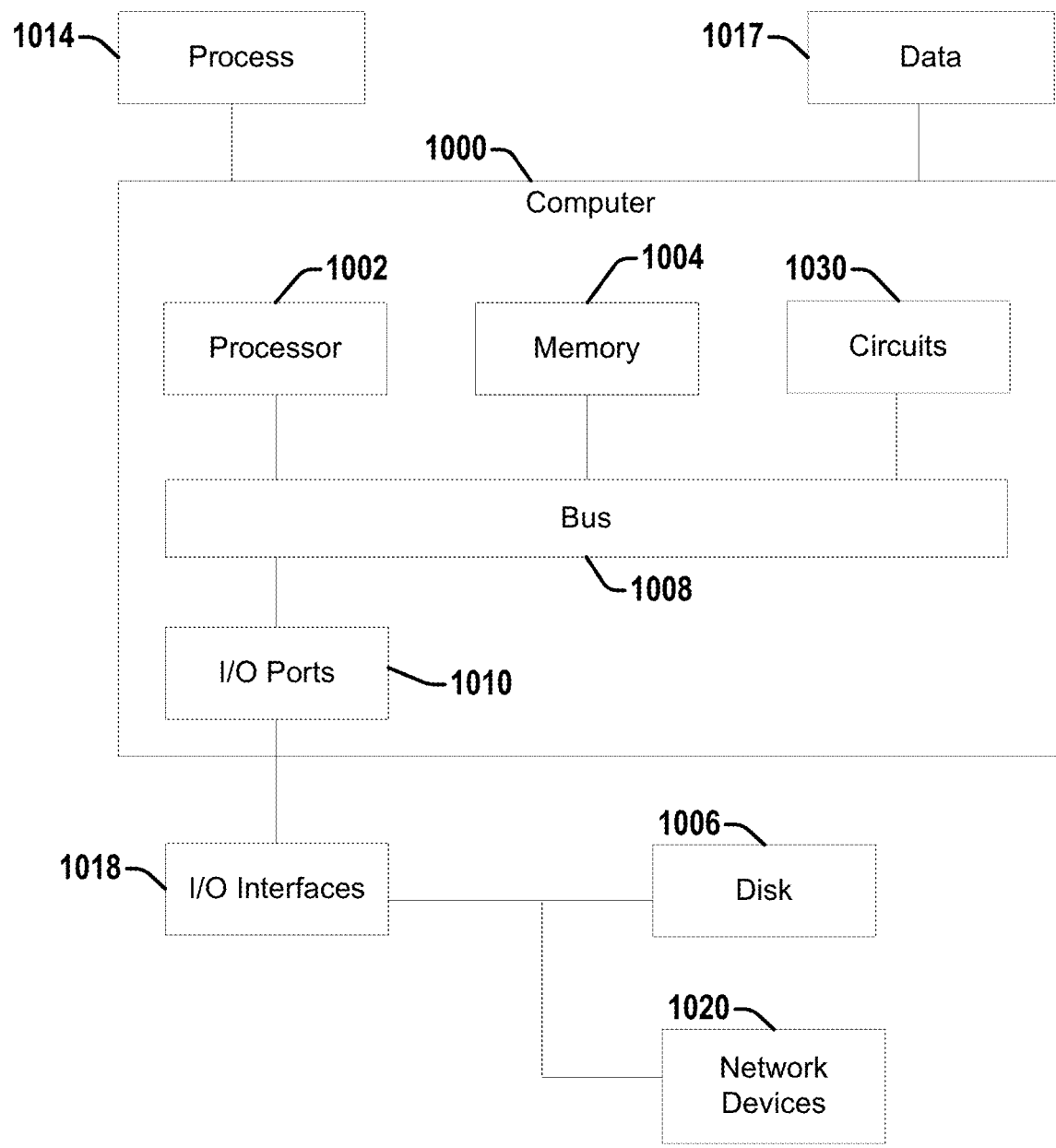
FIG. 10 illustrates an example computer in which embodiments described herein may operate.

FIG. 10 illustrates an example computer 1000 in which example methods illustrated herein can operate and in which example methods, apparatus, circuits, operations, or logics may be implemented. In different examples, computer 1000 may be part of a lung nodule classification system or apparatus, a CT system, an MRI system, a digital whole slide scanner, may be operably connectable to a lung nodule classification system or apparatus, a CT system, an MRI system, or a digital whole slide scanner.

Computer 1000 includes a processor 1002, a memory 1004, and input/output (I/O) ports 1010 operably connected by a bus 1008. In one example, computer 1000 may include a set of logics or circuits 1030 that perform operations for or a method of distinguishing MIA or AIS nodules from invasive adenocarcinoma using a machine learning classifier. Thus, the set of circuits 1030, whether implemented in computer 1000 as hardware, firmware, software, and/or a combination thereof may provide means (e.g., hardware, firmware, circuits) for distinguishing MIA or AIS nodules from invasive adenocarcinoma. In different examples, the set of circuits 1030 may be permanently and/or removably attached to computer 1000.

Processor 1002 can be a variety of various processors including dual microprocessor and other multi-processor architectures. Processor 1002 may be configured to perform operations or steps of methods claimed and described herein. Memory 1004 can include volatile memory and/or non-volatile memory. A disk 1006 may be operably connected to computer 1000 via, for example, an input/output interface (e.g., card, device) 1018 and an input/output port 1010. Disk 1006 may include, but is not limited to, devices like a magnetic disk drive, a tape drive, a Zip drive, a flash memory card, or a memory stick. Furthermore, disk 1006 may include optical drives like a CD-ROM or a digital video ROM drive (DVD ROM). Memory 1004 can store processes 1014 or data 1017, for example. Data 1017 may, in one embodiment, include medical imagery, including digitized CT imagery, including imagery of lung nodules. Disk 1006 or memory 1004 can store an operating system that controls and allocates resources of computer 1000.

Bus 1008 can be a single internal bus interconnect architecture or other bus or mesh architectures. While a single bus is illustrated, it is to be appreciated that computer 1000 may communicate with various devices, circuits, logics, and peripherals using other buses that are not illustrated (e.g., PCIE, SATA, Infiniband, 1394, USB, Ethernet).

Computer 1000 may interact with input/output devices via I/O interfaces 1018 and input/output ports 1010. Input/output devices can include, but are not limited to, CT systems, MRI systems, digital whole slide scanners, an optical microscope, a keyboard, a microphone, a pointing and selection device, cameras, video cards, displays, disk 1006, network devices 1020, or other devices. Input/output ports 1010 can include but are not limited to, serial ports, parallel ports, or USB ports.

Computer 1000 may operate in a network environment and thus may be connected to network devices 1020 via I/O interfaces 1018 or I/O ports 1010. Through the network devices 1020, computer 1000 may interact with a network. Through the network, computer 1000 may be logically connected to remote computers. The networks with which computer 1000 may interact include, but are not limited to, a local area network (LAN), a wide area network (WAN), or other networks, including the cloud.

Examples herein can include subject matter such as an apparatus, a lung nodule classification system, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for classifying lung nodules, according to embodiments and examples described.

Example 1 is a non-transitory computer-readable storage device storing computer-executable instructions that when executed control a processor to perform operations, the operations comprising: accessing a radiological image of a region of lung tissue, where the radiological image includes a ground glass (GGO) nodule; defining a tumoral region by segmenting the GGO nodule, where defining the tumoral region includes defining a tumoral boundary; defining a peri-tumoral region based on the tumoral boundary; extracting a set of radiomic features from the peri-tumoral region and the tumoral region; providing the set of radiomic features to a machine learning classifier trained to distinguish minimally invasive adenocarcinoma (MIA) and adenocarcinoma in situ (AIS) from invasive adenocarcinoma; receiving, from the machine learning classifier, a probability that the GGO nodule is invasive adenocarcinoma, where the machine learning classifier computes the probability based on the set of radiomic features; generating a classification of the GGO nodule as MIA or AIS, or invasive adenocarcinoma, based, at least in part, on the probability; and displaying the classification.

Example 2 comprises the subject matter of any variation of any of example(s) 1, where the radiological image is a non-contrast computed tomography (CT) image having a plurality of slices.

Example 3 comprises the subject matter of any variation of any of example(s) 1-2, where the tumoral region has a diameter less than or equal to two centimeters.

Example 4 comprises the subject matter of any variation of any of example(s) 1-3, where the peri-tumoral region is defined by performing a dilation of the tumoral boundary, where the peri-tumoral region includes a plurality of annular rings.

Example 5 comprises the subject matter of any variation of any of example(s) 1-4, where the set of radiomic features includes at least five radiomic features.

Example 6 comprises the subject matter of any variation of any of example(s) 1-5, where the at least five radiomic features includes four tumoral radiomic features, and one peri-tumoral radiomic feature.

Example 7 comprises the subject matter of any variation of any of example(s) 1-6, where the set of radiomic features includes: a tumoral co-occurrence of local anisotropy gradients (CoLIAGe) feature; a first tumoral Haralick feature; a second, different tumoral Haralick feature; a tumoral Gabor feature; and a peri-tumoral CoLIAGe feature.

Example 8 comprises the subject matter of any variation of any of example(s) 1-7, where the peri-tumoral CoLIAGe feature is extracted from a first annular ring extending from the tumoral boundary to 3 mm from the tumoral boundary.

Example 9 comprises the subject matter of any variation of any of example(s) 1-8, where the machine learning classifier is a linear discriminant analysis (LDA) classifier.

Example 10 comprises the subject matter of any variation of any of example(s) 1-9, where the LDA classifier computes the probability with an area under the receiver operating curve (AUC) of at least 0.97, a sensitivity of at least 95.5%, and a specificity of at least 94%.

Example 11 comprises the subject matter of any variation of any of example(s) 1-10 where the machine learning classifier is a diagonal LDA classifier, a quadratic discriminant analysis (QDA) classifier, or a support vector machine (SVM) classifier.

Example 12 comprises the subject matter of any variation of any of example(s) 1-11, the operations further comprising training the machine learning classifier.

Example 13 comprises the subject matter of any variation of any of example(s) 1-12, the operations further comprising testing the machine learning classifier on a multi-institutional testing cohort.

Example 14 comprises the subject matter of any variation of any of example(s) 1-13, the operations further comprising: generating a personalized treatment plan based, at least in part, on the classification; and displaying the personalized treatment plan.

Example 15 is an apparatus for distinguishing lung nodules, comprising: a processor; a memory configured to store a digitized image of a region of tissue that includes a ground glass opacity (GGO) nodule; an input/output (I/O) interface; a set of circuits; and an interface that connects the processor, the memory, the I/O interface, and the set of circuits, the set of circuits comprising: an image acquisition circuit configured to access a diagnostic image of a region of tissue demonstrating a GGO nodule; a segmentation circuit configured to: define a tumoral region by segmenting GGO nodule, where segmenting the GGO nodule includes defining a tumoral boundary; and define a peri-tumoral region based on a dilation of the tumoral boundary; a radiomic feature circuit configured to: extract a set of radiomic features from the peri-tumoral region and the tumoral region; a nodule classification circuit configured to: compute a probability that the GGO nodule is invasive adenocarcinoma based on the set of radiomic features; and generate a classification of the GGO nodule as minimally invasive adenocarcinoma (MIA) or adenocarcinoma hi situ (AIS), or invasive adenocarcinoma, based, at least in part, on the probability; and a display circuit configured to: display the classification.

Example 16 comprises the subject matter of any variation of any of example(s) 15, where the set of radiomic features includes: a tumoral co-occurrence of local anisotropy gradients (CoLIAGe) feature; a first tumoral Haralick feature; a second, different tumoral Haralick feature; a tumoral Gabor feature; and a peri-tumoral CoLIAGe feature.

Example 17 comprises the subject matter of any variation of any of example(s) 15-16, where the nodule classification circuit is configured to compute the probability that the GGO nodule is invasive adenocarcinoma using a linear discriminant analysis (LDA) machine learning approach.

Example 18 comprises the subject matter of any variation of any of example(s) 15-17, where the diagnostic image is a non-contrast computed tomography (CT) image having a plurality of slices, a slice having a thickness.

Example 19 comprises the subject matter of any variation of any of example(s) 15-18, the set of circuits further comprising a training and testing circuit configured to train the nodule classification circuit to compute the probability that the GGO nodule is invasive adenocarcinoma using a set of training images, where a member of the set of training images is acquired using different imaging parameters than the diagnostic image.

Example 20 is a non-transitory computer-readable storage device storing instructions that when executed by a computer control the computer to perform a method, the method comprising: accessing a computed tomography (CT) image of a region of lung tissue, where the CT image includes a ground glass (GGO) nodule, the CT image having a plurality of slices, a slice having a thickness; defining a tumoral region by segmenting the GGO nodule, where defining the tumoral region includes defining a tumoral boundary; defining a peri-tumoral region based on a morphological dilation of the tumoral boundary, where the peri-tumoral region includes at least one annular ring; extracting a set of radiomic features from the peri-tumoral region and the tumoral region, where the set of radiomic features includes a tumoral co-occurrence of local anisotropy gradients (CoLIAGe) feature, a first tumoral Haralick feature, a second, different tumoral Haralick feature, a tumoral Gabor feature, and a peri-tumoral CoLIAGe feature; providing the set of radiomic features to a linear discriminant analysis (LDA) classifier trained to distinguish minimally invasive adenocarcinoma (MIA) and adenocarcinoma in situ (AIS) from invasive adenocarcinoma using a set of training images, where a member of the set of training images is acquired using different imaging parameters than the diagnostic image; receiving, from the LDA classifier, a probability that the GGO nodule is invasive adenocarcinoma, where the machine learning classifier computes the probability based on the set of radiomic features; generating a classification of the GGO nodule as MIA or AIS, or invasive adenocarcinoma, based, at least in part, on the probability; and displaying the classification.

Example 21 comprises an apparatus comprising means for executing any of the described operations of examples 1-20.

Example 22 comprises a machine readable medium that stores instructions for execution by a processor to perform any of the described operations of examples 1-20.

Example 23 comprises an apparatus comprising: a memory; and one or more processors configured to: perform any of the described operations of examples 1-20.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed control a processor to perform operations, the operations comprising:
    accessing a radiological image of a region of lung tissue, where the radiological image includes a ground glass (GGO) nodule;
    defining a tumoral region by segmenting the GGO nodule, where defining the tumoral region includes defining a tumoral boundary;
    defining a peri-tumoral region based on the tumoral boundary;
    extracting a set of radiomic features from the peri-tumoral region and the tumoral region;
    providing the set of radiomic features to a machine learning classifier trained to distinguish minimally invasive adenocarcinoma (MIA) and adenocarcinoma in situ (AIS) from invasive adenocarcinoma;
    receiving, from the machine learning classifier, a probability that the GGO nodule is invasive adenocarcinoma, where the machine learning classifier computes the probability based on the set of radiomic features;
    generating a classification of the GGO nodule as MIA or AIS, or invasive adenocarcinoma, based, at least in part, on the probability; and
    displaying the classification.

2. The non-transitory computer-readable storage device of claim 1, where the radiological image is a non-contrast computed tomography (CT) image having a plurality of slices.

3. The non-transitory computer-readable storage device of claim 1, where the tumoral region has a diameter less than or equal to two centimeters.

4. The non-transitory computer-readable storage device of claim 1, where the peri-tumoral region is defined by performing a dilation of the tumoral boundary, where the peri-tumoral region includes a plurality of annular rings.

5. The non-transitory computer-readable storage device of claim 1, where the set of radiomic features includes at least five radiomic features.

6. The non-transitory computer-readable storage device of claim 5, where the at least five radiomic features includes four tumoral radiomic features, and one peri-tumoral radiomic feature.

7. The non-transitory computer-readable storage device of claim 6, where the set of radiomic features includes:
    a tumoral co-occurrence of local anisotropy gradients (CoLlAGe) feature;
    a first tumoral Haralick feature;
    a second, different tumoral Haralick feature;
    a tumoral Gabor feature; and
    a peri-tumoral CoLlAGe feature.

8. The non-transitory computer-readable storage device of claim 7, where the peri-tumoral CoLlAGe feature is extracted from a first annular ring extending from the tumoral boundary to 3 mm from the tumoral boundary.

9. The non-transitory computer-readable storage device of claim 1, where the machine learning classifier is a linear discriminant analysis (LDA) classifier.

10. The non-transitory computer-readable storage device of claim 9, where the LDA classifier computes the probability with an area under a receiver operating curve (AUC) of at least 0.97, a sensitivity of at least 95.5%, and a specificity of at least 94%.

11. The non-transitory computer-readable storage device of claim 1, where the machine learning classifier is a diagonal LDA classifier, a quadratic discriminant analysis (QDA) classifier, or a support vector machine (SVM) classifier.

12. The non-transitory computer-readable storage device of claim 1, the operations further comprising training the machine learning classifier.

13. The non-transitory computer-readable storage device of claim 12, the operations further comprising testing the machine learning classifier on a multi-institutional testing cohort.

14. The non-transitory computer-readable storage device of claim 1, the operations further comprising:
generating a personalized treatment plan based, at least in part, on the classification; and
displaying the personalized treatment plan.

15. An apparatus for distinguishing lung nodules, comprising:
a processor;
a memory configured to store a digitized image of a region of tissue that includes a ground glass opacity (GGO) nodule;
an input/output (I/O) interface;
a set of circuits; and
an interface that connects the processor, the memory, the I/O interface, and the set of circuits, the set of circuits comprising:
an image acquisition circuit configured to access a diagnostic image of a region of tissue demonstrating a GGO nodule;
a segmentation circuit configured to:
define a tumoral region by segmenting GGO nodule, where segmenting the GGO nodule includes defining a tumoral boundary; and
define a peri-tumoral region based on a dilation of the tumoral boundary;
a radiomic feature circuit configured to:
extract a set of radiomic features from the peri-tumoral region and the tumoral region;
a nodule classification circuit configured to:
compute a probability that the GGO nodule is invasive adenocarcinoma based on the set of radiomic features; and
generate a classification of the GGO nodule as minimally invasive adenocarcinoma (MIA) or adenocarcinoma in situ (AIS), or invasive adenocarcinoma, based, at least in part, on the probability; and
a display circuit configured to:
display the classification.

16. The apparatus of claim 15, where the set of radiomic features includes:
a tumoral co-occurrence of local anisotropy gradients (CoLlAGe) feature;
a first tumoral Haralick feature;
a second, different tumoral Haralick feature;
a tumoral Gabor feature; and
a peri-tumoral CoLlAGe feature.

17. The apparatus of claim 15, where the nodule classification circuit is configured to compute the probability that the GGO nodule is invasive adenocarcinoma using a linear discriminant analysis (LDA) machine learning approach.

18. The apparatus of claim 15, where the diagnostic image is a non-contrast computed tomography (CT) image having a plurality of slices.

19. The apparatus of claim 15, the set of circuits further comprising a training and testing circuit configured to train the nodule classification circuit to compute the probability that the GGO nodule is invasive adenocarcinoma using a set of training images, where a member of the set of training images is acquired using different imaging parameters than the diagnostic image.

20. A non-transitory computer-readable storage device storing instructions that when executed by a computer control the computer to perform a method, the method comprising:
accessing a computed tomography (CT) image of a region of lung tissue, where the CT image includes a ground glass (GGO) nodule, the CT image having a plurality of slices, a slice having a thickness;
defining a tumoral region by segmenting the GGO nodule, where defining the tumoral region includes defining a tumoral boundary;
defining a peri-tumoral region based on a morphological dilation of the tumoral boundary, where the peri-tumoral region includes at least one annular ring;
extracting a set of radiomic features from the peri-tumoral region and the tumoral region, where the set of radiomic features includes a tumoral co-occurrence of local anisotropy gradients (CoLlAGe) feature, a first tumoral Haralick feature, a second, different tumoral Haralick feature, a tumoral Gabor feature, and a peri-tumoral CoLlAGe feature;
providing the set of radiomic features to a linear discriminant analysis (LDA) classifier trained to distinguish minimally invasive adenocarcinoma (MIA) and adenocarcinoma in situ (AIS) from invasive adenocarcinoma using a set of training images, where a member of the set of training images is acquired using different imaging parameters than the CT image;
receiving, from the LDA classifier, a probability that the GGO nodule is invasive adenocarcinoma, where the LDA classifier computes the probability based on the set of radiomic features;
generating a classification of the GGO nodule as MIA or AIS, or invasive adenocarcinoma, based, at least in part, on the probability; and
displaying the classification.

* * * * *